United States Patent [19]

Tanimoto

[11] Patent Number: 4,553,423
[45] Date of Patent: Nov. 19, 1985

[54] GAS DOSER

[75] Inventor: Masahiro Tanimoto, Kyoto, Japan

[73] Assignee: Horiba, Ltd., Kyoto, Japan

[21] Appl. No.: 619,273

[22] Filed: Jun. 11, 1984

[30] Foreign Application Priority Data

Jun. 28, 1983 [JP] Japan .............................. 58-101578[U]

[51] Int. Cl.⁴ .............................................. G01C 17/38
[52] U.S. Cl. ..................................... 73/1 G; 251/207; 137/595
[58] Field of Search ........... 73/1 G, 3, 863.71, 863.72, 73/863.73; 137/595, 625.19; 251/207

[56] References Cited

U.S. PATENT DOCUMENTS

| | | | |
|---|---|---|---|
| 2,889,852 | 6/1959 | Dunlap | 137/625.19 |
| 4,085,618 | 4/1978 | Collins, Jr. | 73/863.73 |
| 4,445,359 | 5/1984 | Smith | 73/1 G |

Primary Examiner—Bernard Nozick
Attorney, Agent, or Firm—Wenderoth, Lind & Ponack

[57] ABSTRACT

A gas doser, including a gas input member, a gas output member and a charge-over rotor therebetween. The input member includes a gas input member having a carrier gas input port, a calibrating gas input port, a first chamber communicating with the carrier gas input port and a second chamber communicating with the calibrating gas input port. The output member has a carrier gas output port and a calibrating gas output port, respectively communicating with a third chamber and a fourth chamber. The rotor has a carrier gas ventilating conduit for providing communication between the first chamber and the third chamber, and calibrating gas measuring conduits for providing communication between the second chamber and the fourth chamber. Opposite ends of the ventilating conduit and the measuring conduits are mutually spaced from each other about the rotor axis at equal distances from the axis. The rotor is successively rotatable between a first position in which the second chamber communicates with the fourth chamber through the ventilating conduit, and second positions in which the first chamber communicates with the third chamber through a successively increasing number of the measuring conduits. With this structure, it is possible to selectively provide doses of calibrating gas in differing predetermined concentrations in a carrier gas simply by adjusting the rotational position of the rotor.

6 Claims, 9 Drawing Figures

GAS DOSER

BACKGROUND OF THE INVENTION

1. Field Of The Invention

The present invention relates to a gas doser to be used in a gas dosing method wherein measuring conduits are filled with a calibrating gas, and its flow passage is changed by a valve whereby a certain quantity of correcting gas of known concentration can be caused to flow into a gas detecting instrument to correct (recalibrate) the instrument.

2. Description Of The Prior Art

In a gas detector such as a gas analysis meter, it is usual to correct (recalibrate) the detector periodically in order to maintain its detecting precision. As one calibration method, it is known to use a gas dosing method wherein a certain quantity of calibrating gas of known concentration is caused to flow into the gas detecting instrument using a carrier gas.

The conventional gas doser previously used in this method is explained with reference to prior art FIGS. 5(a) and 5(b). In a change-over valve A having six change-over ports $P_1-P_6$, a first input port $P_4$ for calibrating gas communicates with connecting port $P_3$ and a measuring pipe B, and calibration gas is caused to flow via the input port $P_4$, port $P_3$, measuring pipe B, port $P_6$, port $P_5$, and outlet EXH in order to fill measuring pipe (tube) B with calibrating gas as shown in FIG. 5(a). Measuring pipe B has been designed previously with a prescribed volume. Accordingly, the volume of calibrating gas filling measuring pipe B is a known quantity. Next, valve A is changed to concurrently block communication between input port $P_4$ and connecting port $P_3$ and provide communication between port $P_3$ and port $P_2$. As a result, carrier gas is fed into port $P_3$ from port $P_2$ as shown in FIG. 5(b), whereby this carrier gas is introduced into measuring pipe B and calibrating gas within measuring pipe B is fed into the detector from port $P_6$ via port $P_1$ by this carrier gas.

However, in this conventional apparatus, "dead space" C (the part disclosed by oblique lines in FIG. 5 (a) (b)) is formed at the connecting part and change-over part of measuring pipe B, which, unless considered, leads to a measuring error. It is therefore necessary to count the previous content of this dead space. However, it has previously been found troublesome to count this dead space.

Further, in the gas detector multiple point calibration with varied calibrating gas concentrations has been made necessary, because, as is illustrated in the graph of detector output versus calibrating gas concentration shown in FIG. 6, even if a correct detector output corresponding to a particular calibrating gas concentration was obtained at point I, if a correct output value was not obtained for point II or point III where the calibrating gas concentration has been varied there is no sense in making the correction. Accordingly, it is necessary to perform multiple point calibration with varied calibrating gas concentrations. However, in the structure illustrated in FIGS. 5(a) and 5(b), since the quantity of calibrating gas which fills measuring pipe B is constant, it is necessary to perform the laborious task of successively substituting a number of pipes B having differing internal volumes in order to obtain multiple point calibration.

SUMMARY OF THE INVENTION

In view of the above, it is an object of the present invention to provide an apparatus for calibrating a gas analyzer, wherein no dead space comes about at the measuring part and change-over part of the gas dosing apparatus. It is a further object of the invention to provide a single simple apparatus which can easily calibrate the detector at multiple points without interchanging parts, by the simple operation of rotating a rotor.

In accordance with the invention, there is provided a gas doser which includes a gas input member having a carrier gas input port and a calibrating gas input port, and further having a first gas chamber communicating with the gas carrier input port and a second chamber communicating with the calibrating gas input port. Also provided is a gas output member having a carrier gas output port and a calibrating gas output port, and further having a third gas chamber communicating with the carrier gas output port and a fourth gas chamber communicating with the calibrating gas output port. A change-over rotor which is rotatable about a longitudinal axis of rotation is disposed between the gas input member and the gas output member. The rotor has a carrier gas ventilating conduit for providing communication between the first gas chamber and the third gas chamber, and a plurality of calibrating gas measuring conduits for providing communication between the second gas chamber and the fourth gas chamber. Opposite ends of the carrier gas ventilating conduit and the calibrating gas measuring conduits are mutually spaced from each other about the longitudinal axis of rotation at equal distances from said axis. The change-over rotor is successively rotatable between a first position in which the second gas chamber communicates with the fourth gas chamber through the carrier gas ventilating duct, and a plurality of second positions in which the first gas chamber communicates with the third gas chamber through a successively increasing number of the calibrating gas measuring conduits.

With this structure, it is possible to selectively provide doses of calibrating gas in differing predetermined concentrations simply by adjusting the rotational position of the rotor.

BRIEF DESCRIPTION OF THE DRAWINGS

These and other aspects of the invention will be better understood from the following detailed description of the preferred embodiments when taken with the accomanying drawings in which.

DESCRIPTION OF THE PREFERRED EMBODIMENTS

Details of the present invention will be explained with reference to the drawings as follow.

Figure 1:
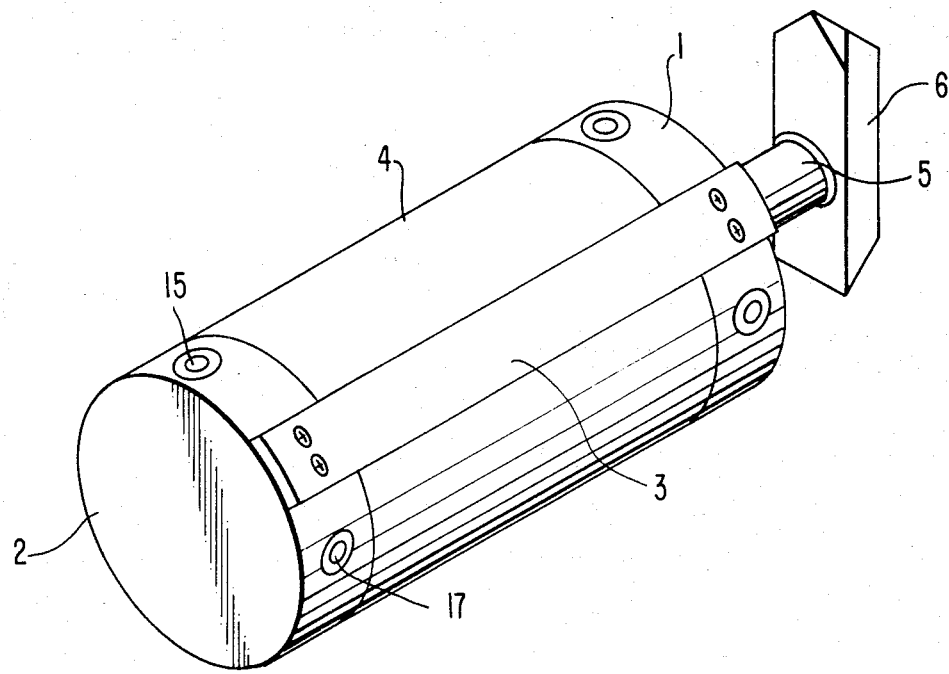
FIG. 1 is an external perspective view of a gas doser in accordance with one embodiment of the present invention.
Figure 3:
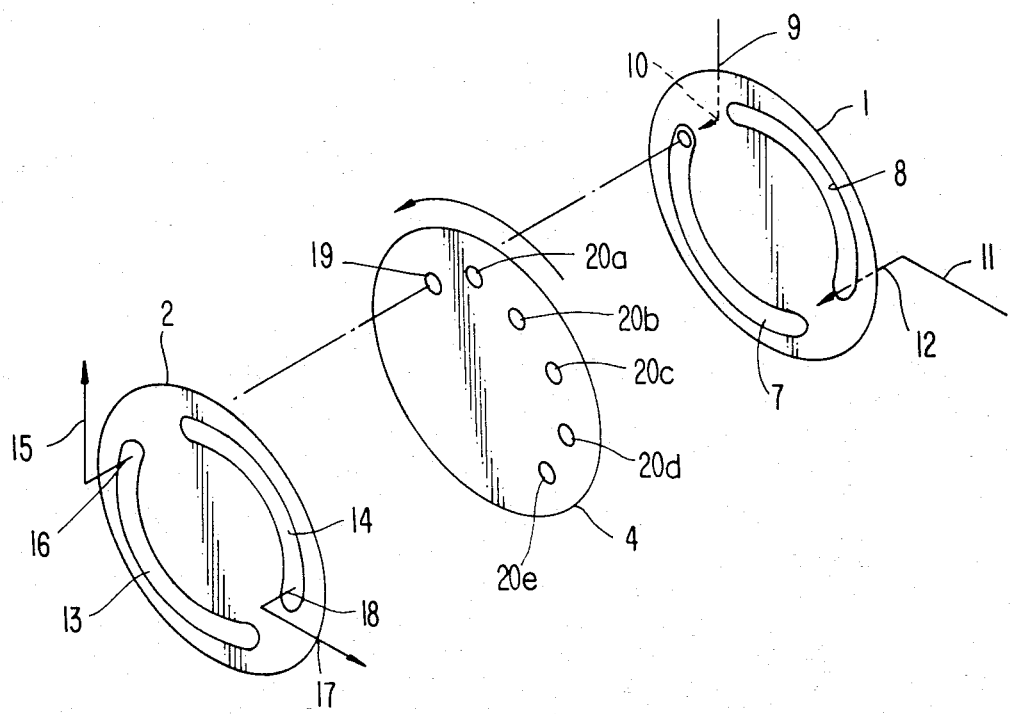
FIG. 3. is an exploded view schematically illustrating the constituents of the gas doser shown in FIG. 2.
Figure 2:
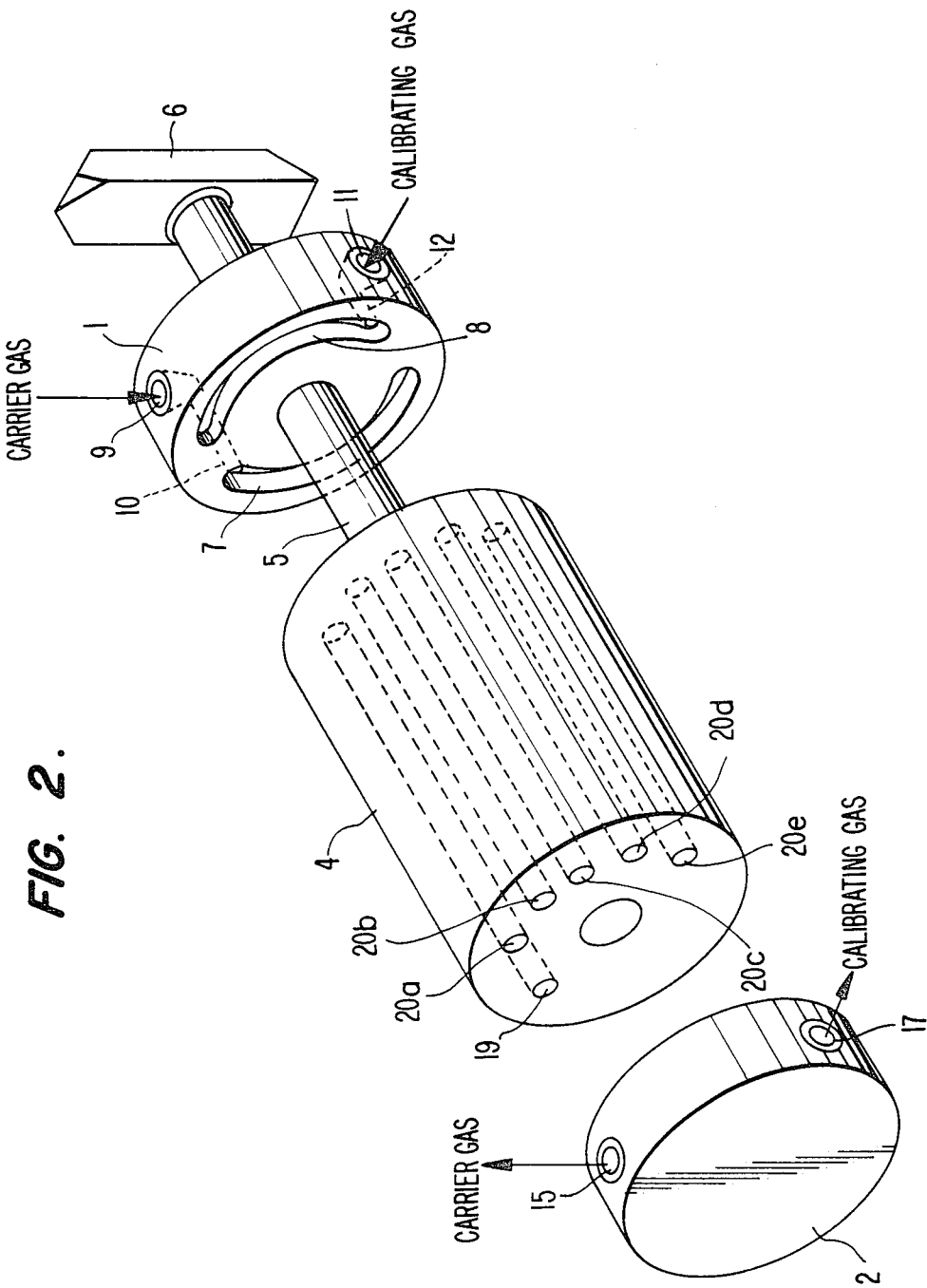
FIG. 2 is an exploded view of the embodiment shown in FIG. 1.

Referring to FIGS. 1-3, a fixed gas input member 1 and a fixed gas output member 2 are connected by a connecting rod 3 to form a fixed body. A change-over rotor 4 is inserted between fixed members 1 and 2. Change-over rotor 4 is slidably supported on one side by the side of gas outlet member 2 so as to be freely rotatable with respect thereto. The other side of change-over rotor 4 is fixed to a rotor shaft 5 which penetrates through gas input member 1 and which is connected to a handle 6 for rotating the rotor 4 through shaft 5. On the face of the rotor which is in sliding contact with fixed gas input member 1, nearly semicircular first and second slot-shaped gas chambers 7 and 8 are provided in diametrically opposed symmetric relation on a circle centered at the axis of rotor shaft 5. Among these, the first gas chamber 7 communicates with a carrier gas imput port 9 provided in fixed gas input member 1 through passage 10, while the second gas chamber 8 communicates with a calibrating gas input port 11 provided in the same element 1 through passage 12. On the other hand, on the face of the rotor 4 in sliding contact with fixed gas output member 2 nearly semicircular third and fourth slot-shaped gas chambers 13 and 14 are provided in diametrically opposed symmetrical relation on a circle centered at the axis of rotor shaft 5 as is apparent from FIG. 3. Among these, the third gas chamber 13 communicates with a carrier gas output port 15 provided in fixed gas output member 2 through a passage 16, while the fourth gas chamber 14 communicates with a calibrating gas output port 17 provided in the same fixed element 2 through a passage 18. The first gas chamber 7 and third gas chamber 13 directly oppose each other in the axial direction of the rotor 4 at coinciding circumferential locations. Similarly, the second gas chamber 8 and the fourth gas chamber 14 are opposed to each other in the axial direction of the rotor 4 at coinciding circumferential locations. The opposing chambers are identical in shape and circumferential extent.

Figure 4A:
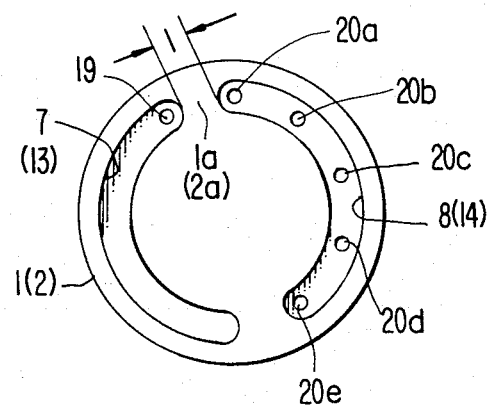
FIGS. 4(a), 4(b) and 4(c) are explanatory views of the rotor.

The change-over rotor 4 is provided with a carrier gas communicating pipe or conduit 19 and multiple (in the drawing five) calibrating gas measuring pipes or conduits 20a through 20e which are located at equal spacing around the periphery of rotor shaft 5. The conduits 20a–20e are located and spaced such that when change-over rotor 4 is set at an initial angular position, carrier gas ventilating conduit 19 mutually communicates with the first gas chamber 7 and third gas chamber 13 as shown in FIGS. 3 and 4(a), and calibrating gas measuring conduits 20a–20e mutually communicate with second gas chamber 8 and fourth gas chamber 14. Further, the adjoining distance l between the first gas chamber 7 and the second gas chamber 8 and the equal adjoining distance l between the third gas chamber 13 and the fourth gas chamber 14 are set larger than the diameter of carrier gas ventilating conduit 19 and calibrating gas measuring conduits 20a–20e, and smaller than the respective spacing between adjoining ones of these conduits 19 and 20a–20e.

Figure 4B:
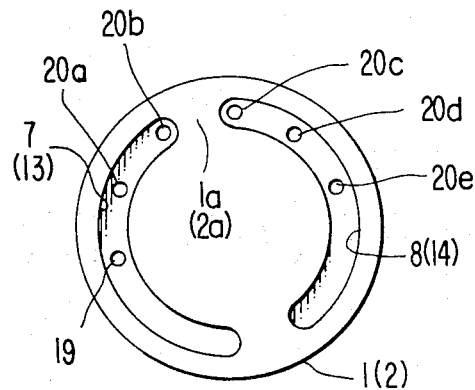

After change-over rotor 4 has been set at an initial period position shown in FIG. 4(a), if sources of carrier gas and calibrating gas are respectively connected to input ports 9 and 11, carrier gas only is fed to the detector via input port 9, passage 10, first gas chamber 7, carrier gas ventilating conduit 19, third gas chamber 13, passage 16 and output port 15. Similarly, during this period, calibrating gas is discharged via input port 11, passage 12, second gas chamber 8, calibrating gas measuring conduits 20a–20e, fourth gas chamber 14, passage 18 and output port 17. Accordingly, correcting gas is not fed to the detector, but fills each of the calibrating gas conduits 20a–20e. Next, if a selected number of the gas measuring conduits, e.g., two of the calibrating gas measuring conduits 20a and 20b, are then caused to communicate with first gas chamber 7 and third gas chamber 13 as shown in FIG. 4(b), by turning change-over rotor 4, e.g. two increments, calibrating gas in an amount equivalent to the volume of these (2) calibrating gas measuring conduits (20a and 20b) is fed to the detector from carrier gas output port 15 through appropriate carrier gas ventilating tubes. In this way, the detector can be calibrated at calibrating gas concentrations determined by the total volume of the selected member, e.g. two, calibrating gas measuring conduits.

The ports 9, 11, 15 and 17 or the gas flow passages (not shown in the drawings) connected to these ports are provided with valves and the valves are opend and closed at particular times during the calibrating operation.

Figure 4C:
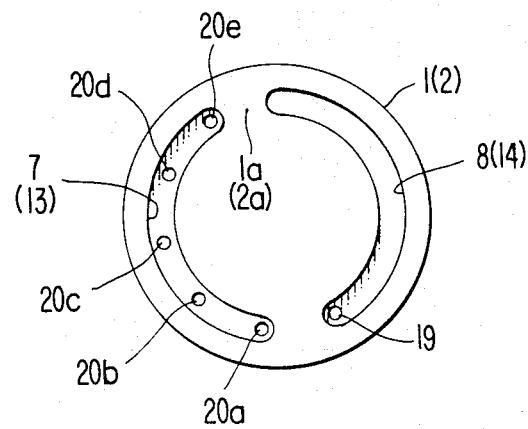
Figure 5A:
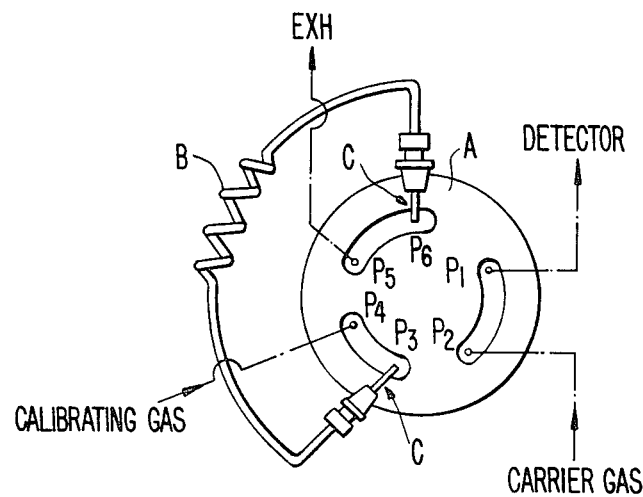
FIGS. 5(a) and 5(b) are schematic illustrations of a conventional gas doser.
Figure 5B:
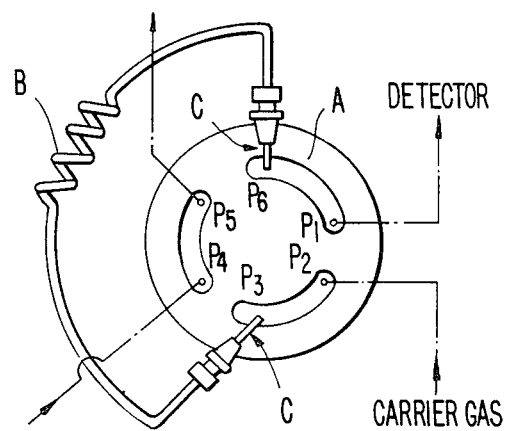
Figure 6:
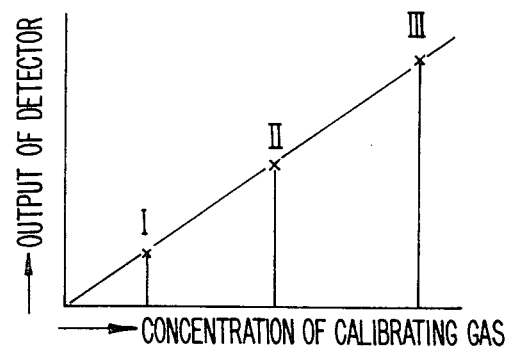
FIG. 6 is a graph illustrating detector output versus calibrating gas concentration for a multiple point calibration.

Similarly, if the amount of calibrating gas corresponding to the volume of all five calibrating gas measuring pipes 20a–20e is fed to the detector by turning change-over rotor 4, five increments as shown in FIG. 4(c), calibrating operation can be performed at a higher calibrating gas concentration. Thus, the calibrating gas concentration can be varied by varying the degree of change-over of change-over rotor 4. Moreover, when calibrating gas measuring conduits 20a–20e are change from communication with second gas chamber 8 and fourth gas chamber 14 to communication with first gas chamber 7 and third gas chamber 13, since the end faces of calibrating gas measuring conduits 20a–20e are flush in respective sliding contact with the end faces 1a and 2a of fixed members 1 and 2, only the amount of gas filling the interior of calibrating gas measuring conduits 20a–20e are brought into the ventilating course of the carrier gas. Moreover, since the internal capacity of each of the calibrating gas measuring conduits 20a–20e is a known volume, exact calibrating gas concentrations can be obtained by setting the internal capacity of calibrating gas measuring conduits, without the need to consider an extra quantity of calibrating gas equivalent to a dead space as was previously necessary.

Multiple point calibration can be performed in which more than one correction is performed with calibrating gas stored in calibrating gas measuring conduits 20a–20e from a single filling. For example, if the first correction is performed by feeding calibrating gas from only one measuring pipe to the detector, then a second correction can be performed by feeding calibration gas from two or three other of the measuring conduits.

In accordance with another embodiment of the invention, multiple point calibration can be performed while varying the calibrating gas concentration by a combination of using selected numbers of calibrating gas measuring conduits 20a–20e, and by utilizing calibrating gas measuring pipes which have differing internal volumes (i.e. varying the diameter of conduits 20a–20e). Thus, more complicated or complete multiple point calibrations can be performed.

The effects of the invention may be similar to as follows:

1. Since calibrating gas measuring conduits are brought into communication with the carrier gas ventilating course after their end faces are slid along the contacting faces of the fixed members 1 and 2 into communication with gas chambers 7 and 13 by rotation of change-over rotor 4, exact amounts of calibrating gas corresponding to the internal volume of the measuring conduits can be fed to the detector, therefore calibration with exact calibrating gas concentrations is possible, and since no dead space is brought about, such dead space can be neglected from the capacity during design, and the manufacture of the gas doser is thereby simplified.

2. Since multiple calibrating gas measuring conduits provided circumferentially on the change-over rotor are concurrently filled with calibrating gas, the calibrating gas concentration can be selected simply by adjustment of the angular position of the change-over rotor. Further, more than one correction can be made from a single filling of the measuring conduits with the calibrating gas.

3. Since the doser is simple in construction comprising a gas input member, a gas output member and a change-over rotor to be rotated relative to these members, reliability of the calibrating procedure can be improved and the manufacturing cost of the doser can be reduced.

4. The doser can be combined with an index mechanism to provide automatic indexing of the rotor and automatic calibration of the gas detector.

While only one preferred embodiment of the invention has been discussed in detail above, various changes and modifications will be readily apparent to those skilled in the art, and the scope of the invention is therefore only to be limited by the appended claims.

What is claimed is:

1. A gas doser, comprising
   a gas input member having a carrier gas input port and a calibrating gas input port, and having a first gas chamber communicating with said carrier gas input port and a second gas chamber communicating with said calibrating gas input port;
   a gas output member having a carrier gas output port and a calibrating gas output port, and having a third gas chamber communicating with said carrier gas output port and a fourth gas chamber communicating with said calibrating gas output port; and
   a change-over rotor rotatable about a longitudinal axis of rotation, disposed between said gas input member and said gas output member, having a carrier gas ventilating conduit for providing communication between said first gas chamber and said third gas chamber and a plurality of calibrating gas measuring conduits for providing communication between said second gas chamber and said fourth gas chamber, opposite ends of said carrier gas ventilating conduit and said plurality of calibrating gas measuring conduits being mutually spaced from each other about said longitudinal axis of rotation equal distances from said axis, said change-over rotor being successively rotatable between a first position in which said second gas chamber communicates with said fourth gas chamber through said carrier gas ventilating conduit and a plurality of second positions in which said first gas chamber communicates with said third gas chamber through a successively increasing number of said plurality of calibrating gas measuring conduits.

2. A gas doser as in claim 1, wherein said gas measuring conduits have differing internal volumes for holding differing volumes of calibrating gas.

3. A gas doser as in claim 1, wherein said successively increasing number increases incrementally by one from one to the total number of said plurality of calibrating gas measuring conduits as said rotor is incrementally rotated through said plurality of second positions.

4. A gas doser as in claim 1, wherein each of said plurality of calibrating gas measuring conduits extends between first and second faces of said change-over rotor, said gas input member and said gas output member respectively having gas input and gas output faces respectively having said first and third gas chambers and said second and fourth gas chambers exposed thereon, said first and second faces respectively slidably contacting said gas input face and said gas output face.

5. A gas doser as in claim 4, wherein each of said plurality of calibrating gas measuring conduits extends parallel said axis of rotation, said first and second faces being at opposite ends of and extending perpendicular to said axis of rotation in confronting relation to said gas input and gas output faces, respectively.

6. A gas doser as in claim 5, wherein said first gas chamber and said second gas chamber are located with respect to said axis of rotation at respectively diametrically symmetrical positions, and said third and fourth gas chambers are respectively of the same shape and circumferential length about said axis and located at the same circumferential location as said first and second gas chambers.

* * * * *